United States Patent [19]

Williams, Jr.

[11] Patent Number: 5,027,832
[45] Date of Patent: Jul. 2, 1991

[54] SURGICAL DRAPE SUPPORT APPARATUS

[76] Inventor: John W. Williams, Jr., 4203 Belfort Rd., Suite 150, Jacksonville, Fla. 32216

[21] Appl. No.: 465,047
[22] Filed: Jan. 5, 1990
[51] Int. Cl.⁵ .............................................. A61B 19/00
[52] U.S. Cl. ................................... 128/849; 128/851; 248/100
[58] Field of Search ............................ 128/849–854; 248/100, 231.5, 101, 103, 104

[56] References Cited

U.S. PATENT DOCUMENTS

| | | | |
|---|---|---|---|
| 2,451,829 | 10/1948 | Hightower | 248/100 |
| 3,220,434 | 11/1965 | Garth | 248/100 |
| 3,859,993 | 1/1975 | Bitner | 128/849 X |
| 4,122,848 | 10/1978 | Carpel | 128/849 X |
| 4,146,265 | 3/1979 | Ocel et al. | 248/100 X |
| 4,702,445 | 10/1987 | Ivory | 248/100 |
| 4,852,841 | 8/1989 | Sebring | 248/231.5 |
| 4,854,016 | 8/1989 | Rice | 248/231.5 X |
| 4,890,628 | 1/1990 | Jackson | 128/849 |
| 4,936,318 | 6/1990 | Schoolman | 128/847 |

Primary Examiner—Robert A. Hafer
Assistant Examiner—Kerry Owens
Attorney, Agent, or Firm—Thomas C. Saitta

[57] ABSTRACT

A support and drape apparatus which is attached to an operating room table for retaining fluid excess during surgery. The support is a framework of two lateral members and a transverse member attached to each lateral member such that a perimeter is formed in conjunction with the operating room table. A waterproof drape is placed on the framework such that a pocket retains the fluid. The drape may have a water permeable drain. The lateral members have a substantially rigid portion connected to a flexible portion and the transverse member is relatively flexible throughout its length, which allows the framework to give to allow movement by the surgeon without destroying the integrity of the pocket.

18 Claims, 2 Drawing Sheets

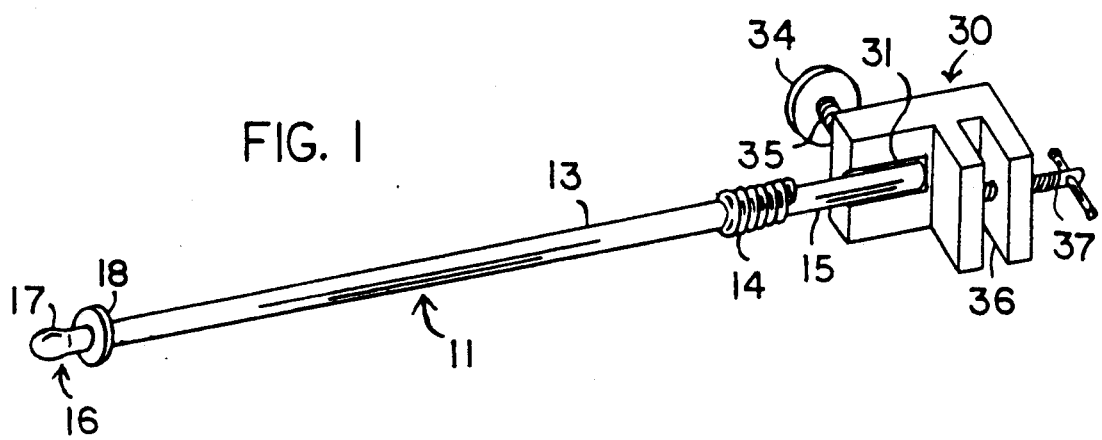
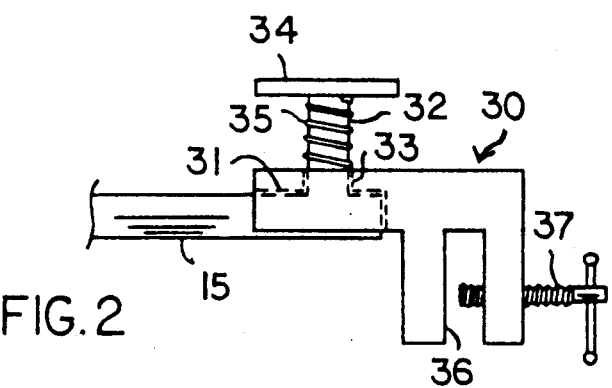
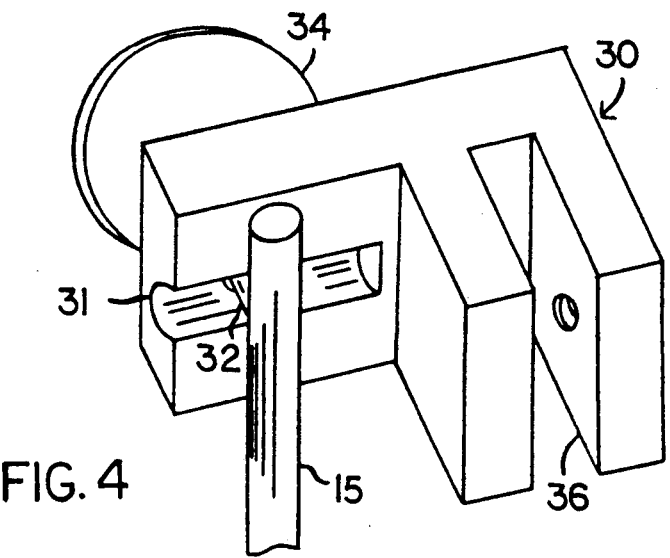

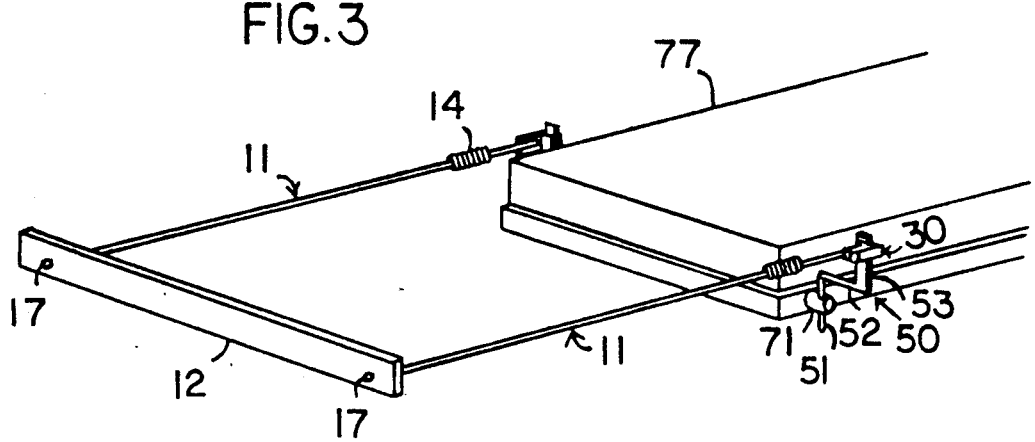
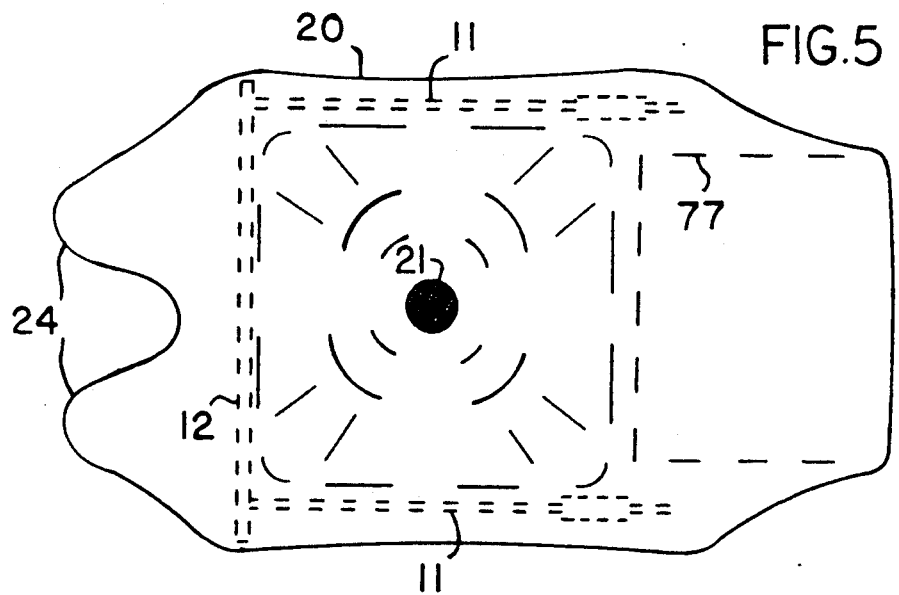
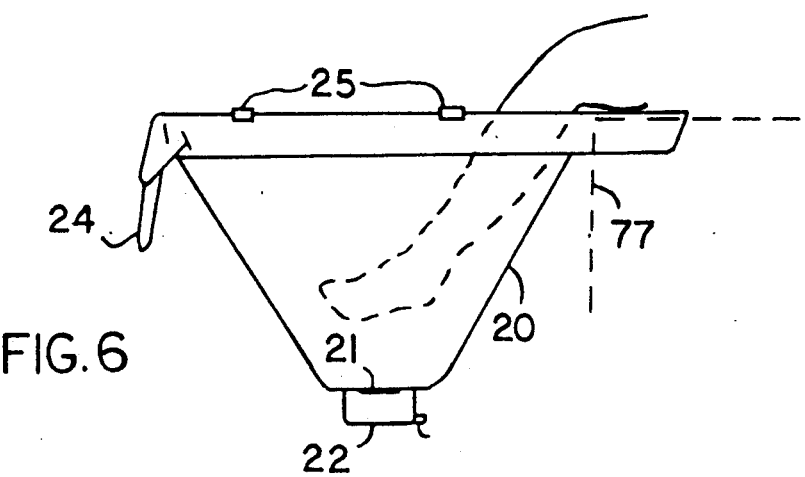

SURGICAL DRAPE SUPPORT APPARATUS

BACKGROUND OF THE INVENTION

The invention relates generally to the field of drape support apparatus used during surgical procedures which involve significant amounts of fluid drainage. More particularly, the invention relates to the field of surgical drape and support apparatus used in knee surgery, where the drape acts as a reservoir or drain for retention of excess fluids utilized during the surgery procedure.

In many surgery procedures, and in particular in arthroscopic knee surgery, large amounts of fluid are utilized during the operation. For arthroscopic knee surgery, where the surgical procedure is accomplished with instruments inserted through small incisions in the knee area as opposed to cutting a large incision to allow access, fluids such as saline solutions are introduced into the knee area to distend the soft tissue and create space for the surgeon to manipulate the instruments. This fluid is forced into the area under sufficient pressure to maintain the knee in the distended form. During the procedure, some of the fluid escapes from the knee cavity through the instrument incisions. Also, at various points in the operation the surgeon may release some of the fluid to adjust the amount of distension.

For significant operations, it is not unknown to use 75 liters or more of fluid in a single procedure. This huge amount of fluid is often allowed to flow into drains on the floor of the operating room. This technique results in unsafe conditions as the floors can become slippery with excess or splattered fluid. Some surgeons even wear waterproof boots because of the large amount of fluid present on the operating room floor. One technique used to attack this problem is to place a large suction pad on the floor to absorb and remove the excess fluid, but this method does not alleviate splattering and overflow when large amounts of fluid are flushed. The pad itself can interfere with footing. Another method sometimes employed is to use a surgical drape attached to the thigh of the patient and the main surgical drape to form a small pouch. However, there is no structural support to maintain the pouch in optimum shape and position, which when coupled with the small size of the pouch results in significant fluid spillage and loss.

The invention solves the problems associated with the large volume of fluid required in operations of this type by providing a structural framework to support a drape to retain the fluid for removal. The drape may include a drain and receptacle, and may be shaped for attachment to the surgeon. The structural framework is sufficiently rigid to maintain the drape in the desired configuration even when retaining large amounts of fluid, yet is also flexible enough to allow the surgeon some degree of movement. The invention thus prevents fluid from splattering and the fluid is kept from the floor, while the framework does not restrict the mobility of the surgeon during the operation.

It is an object of this invention to provide a drape support apparatus which retains excess fluid used during surgical procedures, especially surgeries involving the knee.

It is a further object to provide such an apparatus that allows the fluid to be drained or suctioned out during the operation.

It is a further object to provide such an apparatus where the support framework is rigid enough to adequately support the drape and fluid, but is also flexible enough to allow movement by the surgeon.

It is a further object to provide such an apparatus which is readily attachable to standard operating tables.

It is a further object to provide such an apparatus which is easily set into position when required.

BRIEF SUMMARY OF THE INVENTION

The invention comprises a support framework and drape adapted to be attached to a standard operating table. The support framework comprises two lateral members, each having a rigid major portion joined to a flexible portion. The lateral members are joined to attachment means, so that each can be affixed to opposing sides of an operating table. For example, the lateral member may comprise a stainless steel pole joined to a heavy metal spring and a mounting bracket. Preferably the mounting bracket allows the pole to be pivoted in and out of position after it has been attached to the operating table. A transverse member is detachably affixed to the free ends of each of the lateral members. The transverse member is substantially rigid to support the drape in the vertical direction, while at the same time being flexible in the direction parallel to the longitudinal axis of the lateral members. For example, the transverse member may be constructed from a bar-shaped dense foam material, rectangular in cross-section, and attached between the lateral members such that the larger cross-sectional dimension is vertical and the thinner dimension is parallel to the longitudinal axis of the lateral members. The drape, comprised of any flexible, waterproof material, is suspended between the two lateral members and the transverse member such that a pocket is formed, and the drape is attached by clamps or other means to the framework. A suction device can be used to remove the fluid which collects in the drape pocket, or the drape may further comprise a drain and receptacle which allows the fluid to flow out of the drape, where it ca be removed through attached conduits. Additionally the drape may be attached to the surgeon by various fastening means to further insure that no fluid will accidentally be spilled. The construction of the framework allows it to give and flex as the surgeon changes position, while the integrity of the reservoir formed by the drape is maintained.

BRIEF DESCRIPTION OF THE DRAWINGS

FIG. 1 is a perspective view of a lateral support member and the attachment means.

FIG. 2 is a top plan view of a portion of the lateral support member, showing the attachment means and connector end.

FIG. 3 is a perspective view showing the framework apparatus attached to an operating table using the extension members.

FIG. 4 is a perspective view showing a portion of a lateral support member, with the lateral support member situated in the downward position relative to the attachment means.

FIG. 5 is a top view of the drape positioned on the framework and the operating table.

FIG. 6 is a side view of the drape in position on the framework.

DETAILED DESCRIPTION OF THE INVENTION

During arthroscopic knee surgery, the patient is positioned so that the lower portion of the leg to be operated on extends beyond the end of an operating table. This allows the surgeon to manipulate the knee joint as necessary by shifting the patient's lower leg. The surgeon usually sits or stands facing the patient with the patient's foot resting against the surgeon's body. The surgeon can then manipulate the knee joint by varying his own body position relative to the patient. A large amount of fluid is used to distend the patient's knee during an operation. The invention comprises a support framework drape apparatus which is attached to the operating table and extends outwardly therefrom, the support framework forming a perimeter around the patient's leg such that the drape forms a pocket underneath the patient's leg to retain for removal the fluids used during the operation. The support framework is rigid enough to carry the weight of the drape and fluids, yet is flexible enough to allow the surgeon to move against it without affecting the integrity of the perimeter and pocket formed in the drape reservoir.

The apparatus comprises in general two lateral support members 11 and a transverse support member 12 which form a support framework substantially parallel with the floor, and attachment means 30 for affixing the apparatus to an operating room table or other fixed object such that the two lateral members 11 extend outwardly from the end of the table on either side of the patient, with the transverse member 12 creating a closed perimeter to support a drape 20. Drape 20, made of any suitable flexible, waterproof material, is of a size and configuration suitable to extend over the support framework members and form a deep pocket. Standard rectangular surgical drapes can be used, or drape 20 may be specially pre-formed to include a large pocket.

With reference to FIG. 1, one of the two lateral members 11 is shown with attachment means 30. Lateral member 11 is approximately 28 inches in length and comprises an elongated, relatively rigid rod portion 13, a flexible means portion 14, a connector end 15, and a tip 16. The rod 13 is preferably made of stainless steel, but any suitable material capable of supporting the combined weight of the drape 20 and fluids may be used. The rigid rod portion 13 is preferably circular in cross-section with a diameter of approximately three-eighths inches, but any suitable configuration could be used. One end of the rod 13 is connected to a flexible means portion, which is preferably a heavy gauge spring 14 several inches in overall length also made of stainless steel. The gauge of the spring 14 must be of sufficient size to maintain the rod 13 in a horizontal position when it is supporting the weight of the drape 20 and fluids, yet must also allow some degree of flexing when the surgeon leans against the apparatus. Extending from the opposite end of spring 14 is the connector end 15, which is also preferably formed from stainless steel rod. The connector end 15 connects the rod 13 and spring 14 to an attachment means 30 which is used to attach the apparatus to the side of an operating room table. At the opposite end of the lateral member 11, the rod 13 ends in a tip 16 adapted to allow easy connection and disconnection of the transverse member 12. As shown, the tip 16 is preferably shaped in the form of a knob 17 with a stop flange 18. This construction allows the tip 16 to be inserted into an aperture in the transverse member 12, the knob 17 acting to retain the transverse member 12 on the lateral member 11 and the flange 18 acting to prevent the transverse member 12 from sliding down onto the rod 13. The rigid rod portion 13 of lateral member 11 supports the drape 20, while the flexible spring 14 allows the framework of the apparatus to give so that the surgeon is not restricted by the framework during the operation.

Attachment means 30 can be of any structure allowing the lateral members 11 to be affixed to the sides of an operating room table or other fixed structure such that the support framework will be maintained in a horizontal position when in use. The preferred embodiment of attachment means 30 has a release means to allow lateral member 11 to be pivoted out of horizontal when required. Attachment means 30, as also shown in FIG. 2, has a channel 31 which is adapted to receive the connector end 15 of lateral member 11. Connector end 15 has a leg 32 extending perpendicularly from the main longitudinal axis. This leg 32 extends through an aperture 33 in attachment means 30 and ends in a cap 34. Between the cap 34 and the body of the attachment means 30, leg 35 is surrounded by a locking spring 35. Locking spring 35 retains the connector end 15 in channel 31. Locking spring 35 allows connector end 15 to be displaced from channel 31 by pressing against cap 34 when it is desired to lower the lateral member 11 out of the horizontal position. The main body of attachment means 30 is F-shaped, with the leg of the "F" containing channel 31. The arms of the "F" form slot 36, which is adapted in conjunction with screw 37 to grasp extension members 50 for attachment to an operating room table.

With reference now to FIG. 3, the two lateral members 11 are shown attached to operating table 77 by the use of extension members 50. The extension members 50 are not required, but their use allows for a greater framework perimeter. Extension members 50 comprise a vertical rod portion 51 which fits into the standard apertured brackets 71 found o operating room tables, a horizontal rod portion 52 which extends the apparatus out from the edges of the operating room table 77, and a vertical connection bar 53 which is grasped by attachment means 30. The attachment means 30 of lateral members 11 are connected to the extension members 50 by inserting the connection bar 53 into slot 36 and tightening screw 37. In this manner, the lateral members 11 are set in the horizontal position extending on either side away from the end of the operating table 77. The extension members 51 are preferably constructed of stainless steel, and may be of differing sizes to suit particular table sizes or needs. The length of the horizontal rod portion 52 may be varied depending on the amount of separation desired between the lateral members 11 and the operating table 77.

Except during the actual operation, it is preferable that the lateral members 11 be positioned out of the way so as not to interfere with the medical personnel and set up procedures. This is accomplished, as shown in FIG. 4, by pressing on cap 34 to compress locking spring 35, which allows connector end 15 to be displaced from within channel 31. Lateral member 11 can now be pivoted around leg 32 so as to point toward the floor. After the patient has been positioned, the lateral members 11 can be returned to the horizontal position by rotating in the opposite direction until connector end 15 snaps into channel 31. Because of this construction, the lateral members 11 and attachment means 30 can remain on the operating table 77 without need for reconnection during every operation.

Referring again to FIG. 3, transverse member 12 is shown attached to both lateral members 11. Transverse member 12 is preferably constructed of a bar-shaped, substantially dense foam material, with a rectangular cross section. Openings 19 are positioned at each end through the short dimension of transverse member 12 to receive the tips 16 of the lateral members 11. Transverse member 12 must by substantially rigid in the vertical direction to support the drape 20 and accumulated fluids, but it is preferable that transverse member 12 be continuously flexible along its length in the direction along the longitudinal axis of the lateral members 11. The rectangular configuration allows transverse member 12 to be sufficiently rigid in the vertical direction, while allowing it to flex in the horizontal direction. This allows the surgeon to move closer to the patient when required, since the transverse member 12 and lateral members 11 will flex and deform. This deformation maintains the general pocket shape and perimeter of the drape 20 to prevent splashing and control the fluid excess.

To collect the fluid during the operation, a waterproof drape 20 is positioned over the framework created by the table 77, the two lateral members 11, and the transverse member 19, as seen in FIGS. 5 and 6. Drape 20 is temporarily attached to the framework by clamps 25 or similar means, with enough excess material in the center to form a deep pocket below the patient's leg and foot. Standard surgical drapes 20 may be used, in which case a suction tube is placed into the lowest portion of the pocket and the fluid is pumped out for disposal. Preferably, a specifically designed drape 20 is utilized. This drape 20 has a drain 21 located in the bottom-most portion of the pocket, drain 21 being made from any suitable type netting, gauze, felt or other water-permeable material. Below drain 21, receptacle bag 22 retains the excess fluid for removal through valve 23 by gravity flow or suitable suction means. This drape 20 can be manufactured with a pre-formed large pocket. In a further preferred embodiment, drape 20 is shaped with means to attach the drape 20 directly to the surgeon, such as tie flaps 24, which allow the drape 20 to be wrapped around the waist of the surgeon and fastened by suitable fastening means, such as Velcro or snap fasteners. This construction further insures the integrity of the system during movement of the surgeon.

To utilize the apparatus of the invention, the extension members 50 are attached to the standard brackets 71 near the end of the operating table 77 on either side. The attachment means 30 of each lateral member 11 is connected to an extension member 50, and the lateral members are rotated to the downward position. The drape 20 is then secured to the table 77 so as to cover the extension members 50 and the attachment means 30, and the patient is positioned. The lateral members 11 are then rotated to the horizontal position, the transverse member 12 is attached to the ends of each lateral member 11 and the drape 20 is clamped over and onto the lateral members 11 and the transverse member 12. A suction pump or other fluid removal means is attached to the valve 23 of the receptacle bag 22 for removal of the fluid. When the surgeon is in position, the tie flaps 24 of the drape 20 are fastened around his waist. The excess fluid utilized in the operation will now be captured and drained by the apparatus, while the flexibility of the support framework does not interfere with the surgeon.

The above illustrations are by way of example only, and substitutions and equivalents will be obvious to those skilled in art. The full scope and definition of the invention therefore, is to be a set forth in the following claims.

I claim:

1. An apparatus for supporting a flexible, waterproof drape to retain fluid during surgery, adapted to be attached to an operating room table having opposite sides, comprising:
   (A) a pair of lateral support members comprising a relatively rigid portion connected to a flexible means portion, whereby said lateral support members are flexible in any direction;
   (B) a pair of attachment means for attaching said lateral support members to opposite sides of said operating room table, said attachment means being adapted to maintain said lateral members in a horizontal position;
   (C) a transverse support member attached to each of said lateral support members, where said transverse support member is rigid in the vertical direction and flexible in the horizontal direction;
   whereby said lateral support members and said transverse support member form a framework in conjunction with said operating room table to support said drape to retain fluid during surgery.

2. The apparatus of claim 1, where said flexible means portion is a spring.

3. The apparatus of claim 1, where said transverse support member is made of a substantially dense foam material.

4. The apparatus of claim 1, wherein said attachment means further comprise release means adapted to pivot said lateral support members out of horizontal position.

5. The apparatus of claim 1, further comprising extension members to separate said attachment means from said operating room table.

6. The apparatus of claim 1, where said lateral support members are made of stainless steel.

7. The apparatus of claim 1, where said transverse support member is removably attached to said lateral support members.

8. An apparatus for retaining fluid during surgery, adapted to be attached to an operating room table having opposite sides, comprising:
   (A) a pair of lateral support members having a relatively rigid portion connected to a flexible means portion, whereby said lateral support members are flexible in any direction;
   (B) a pair of attachment means for attaching said lateral support members to opposite sides of said operating room table, said attachment means being adapted to maintain said lateral support members in a horizontal position;
   (C) a transverse support member attached to each of said lateral support members, where said transverse support member is rigid in the vertical direction and flexible in the horizontal direction;
   (D) flexible, waterproof drape means of sufficient size to form a pocket when placed on said lateral support members and said transverse support member;
   whereby said lateral support members and said transverse support member form a framework in conjunction with said operating room table to which said drape means is attached to retain fluid during surgery.

9. The apparatus of claim 8, where said flexible means portion is a spring.

10. The apparatus of claim 8, where said drape means further comprises a water permeable drain means.

11. The apparatus of claim 10, where said drape means further comprises a receptacle means attached below said drain means.

12. The apparatus of claim 8, where said drape means has a preformed pocket.

13. The apparatus of claim 12, where said drape means further comprises a water permeable drain means.

14. The apparatus of claim 8, where said drape means further comprises means for attaching said drape means to a surgeon.

15. The apparatus of claim 8, where said attachment means further comprise release means adapted to pivot said lateral support members out of horizontal position.

16. An apparatus for retaining fluid during surgery, adapted to be attached to an operating room table, comprising:
(A) a pair of lateral support members having a relatively rigid portion connected to a flexible means portion;
(B) attachment means for attaching said lateral support members to said operating room table, where said attachment means maintain said lateral support members in a horizontal position, said attachment means further comprising release means adapted to pivot said lateral support members out of the horizontal position; said releases means comprising a channel to receive said lateral support member, a leg member attached to said lateral support member which extends through said attachment means, a locking spring encircling said leg member, and a cap on the end of said leg member, where said lateral support member is pivoted by depressing said cap and locking spring to push said lateral support member out of said channel;
(C) a transverse support member attached to each of said lateral support members;
(D) flexible, waterproof drape means of sufficient size to form a pocket when placed on said lateral support members and said transverse support member;
whereby said lateral support members and said transverse support member form a framework in conjunction with said operating room table to which said drape means is attached to retain fluid during surgery.

17. The apparatus of claim 16, where said flexible means portion is a spring.

18. The apparatus of claim 16, where said drape means further comprises a water permeable drain means.

* * * * *